United States Patent
Yamasaki et al.

(10) Patent No.: US 7,664,311 B2
(45) Date of Patent: Feb. 16, 2010

(54) COMPONENT MOUNTING BOARD INSPECTING APPARATUS

(75) Inventors: Hiroshi Yamasaki, Kanagawa (JP); Hiroshi Ootsuki, Kanagawa (JP); Yutaka Igarashi, Saitama (JP)

(73) Assignee: Sony Corporation, Tokyo (JP)

( * ) Notice: Subject to any disclaimer, the term of this patent is extended or adjusted under 35 U.S.C. 154(b) by 602 days.

(21) Appl. No.: 11/039,902

(22) Filed: Jan. 24, 2005

(65) Prior Publication Data
US 2005/0196996 A1 Sep. 8, 2005

(30) Foreign Application Priority Data
Feb. 9, 2004 (JP) .......................... P2004-032567

(51) Int. Cl.
*G06K 9/00* (2006.01)
(52) U.S. Cl. ....................................... 382/150; 382/149
(58) Field of Classification Search ................. 382/141, 382/149, 150
See application file for complete search history.

(56) References Cited

U.S. PATENT DOCUMENTS

| | | | |
|---|---|---|---|
| 5,134,575 A * | 7/1992 | Takagi ......................... | 382/147 |
| 5,621,811 A * | 4/1997 | Roder et al. ................ | 382/147 |
| 5,719,952 A * | 2/1998 | Rooks ......................... | 382/150 |
| 6,130,959 A * | 10/2000 | Li ................................ | 382/150 |
| 6,167,149 A * | 12/2000 | Tsujikawa et al. ........... | 382/147 |
| 6,259,624 B1 * | 7/2001 | Nobukata ............... | 365/185.03 |
| 6,289,117 B1 * | 9/2001 | Li ................................ | 382/150 |
| 6,317,513 B2 * | 11/2001 | Michael et al. .............. | 382/145 |
| 6,529,624 B1 * | 3/2003 | Kim ............................ | 382/150 |
| 7,233,871 B2 * | 6/2007 | Raymond et al. ............. | 702/83 |
| 2004/0146195 A1 * | 7/2004 | Fukagawa et al. ........... | 382/150 |

FOREIGN PATENT DOCUMENTS

| | | |
|---|---|---|
| JP | 61-288106 | 12/1986 |
| JP | 06-018237 | 1/1994 |
| JP | 10-160426 | 6/1998 |

* cited by examiner

*Primary Examiner*—John B Strege
(74) *Attorney, Agent, or Firm*—Rader, Fishman & Grauer PLLC

(57) ABSTRACT

There is provided a component mounting inspecting apparatus which can automatically set a solder bridge inspection region (an inspection point) and output an optimum inspection result of a solder bridge. The component mounting board inspecting apparatus for inspecting a solder bridge of an electronic circuit board, in which a plurality of electrode pads are formed at predetermined spaced intervals and cream solder is applied on the electrode pads, includes a mechanism for automatically determining a distance between adjacent electrode pads and a mechanism for automatically setting a solder bridge inspection point if the distance between the adjacent electrode pads is equal to or shorter than a threshold value.

8 Claims, 5 Drawing Sheets

COMPONENT MOUNTING BOARD INSPECTING APPARATUS

CROSS REFERENCE TO RELATED APPLICATIONS

The present document is based on Japanese Priority Document JP2004-032567, filed to the Japanese Patent Office on Feb. 9, 2004, the contents of which are incorporated herein by reference.

BACKGROUND OF THE INVENTION

1. Field of the Invention

The present invention relates to a component mounting board inspecting apparatus for inspecting for defects in cream solder printed on an electrode pad of a component mounting board, and, more specifically, inspecting whether there are solder bridges generated between adjacent electrode pads.

2. Description of Related Art

On a component mounting board, such as a printed board for mounting a number of components of a semiconductor device and the like, a number of electrode pads corresponding to the number of electrodes of these components, and a wiring circuit pattern are formed. In order to solder these components cream solder is printed on the electrode pads by a screen printing method, for example. If the cream solder is not suitably printed on the electrode pads, the components cannot be desirably soldered. Therefore, before soldering the components on the component mounting board, the board is inspected for whether or not the cream solder is suitably printed on each electrode pad by the use of a component mounting board inspecting apparatus.

A functional block diagram of such a component mounting board inspecting apparatus is shown in FIG. 4, in which reference numeral 100 indicates a component mounting board inspecting apparatus. The component mounting board inspecting apparatus 100 has an annular illuminating apparatus 110, a camera 120, such as a CCD camera, an image processor 130, a control unit 140, and a result indicator 150.

The illuminating apparatus 110 facilitates observation of a component mounting board B. The camera 120 captures a visual image of the component mounting board B illuminated by the illuminating apparatus 110. The image processor 130 captures the image outputted from the camera 120, and then executes an inspection algorithm. The control unit 140 controls the brightness of the illuminating apparatus 110, and the drives of the illuminating apparatus 110 and the camera 120. The result indicator 150 indicates an obtained inspection result.

A method of determining whether cream solder is suitably printed or not is as follows: the printed state of the cream solder on the component mounting board B is compared with the information captured by the image processor 130, based on the information of printing of cream solder (the printing area of the cream solder, the printing width of the cream solder, and the printing position of the cream solder), which are preset in the component mounting board inspecting apparatus 100.

In the cream solder inspection method, the object to be inspected is solder subjected to reflow, instead of cream solder. This kind of inspection is disclosed in Japanese Patent Application Laid-Open No. 10-160426 (page 1, and abstract), for example.

A variety of electrode pads are formed on the component mounting board B, such that a variety of components, including various semiconductor devices, are mountable thereon. A plurality of electrode pads 1A, 1B, 1C, . . . , are formed in a predetermined array on the component mounting board B, and the pad-to-pad distance of these electrode pads will vary over different portions, as partially shown in FIG. 5 (electrode pads having a large pad-to-pad distance are not shown). Referring to FIG. 5, the pad-to-pad distance of the electrodes pads 1A, 1B, 1C, . . . , which mount, for example, a ball grid array (BGA) type IC and a quad flat package (QFP) type IC, is considerably narrow (or, short), for example, about 500 μm or less. When cream solder S is printed on the electrode pads 1A, 1B, 1C, by a screen printing method, etc., as shown in FIG. 6, it is desirable that the cream solder S is printed so as not to spread beyond the electrode pad 1B. However, as shown in FIG. 7, the cream solder S on a certain electrode pad, for example, the electrode pad 1A, may bridge the electrode pad 1B adjacent to the right side. This is a so-called solder bridge Sb. Needless to say, the occurrence of the solder bridge Sb is undesirable, and hence this must be reliably detected, and the component mounting board B involving the solder bridge Sb must be removed from the line.

Conventionally, in creating an inspection program for detecting the solder bridge Sb between the pads at which a solder bridge Sb is likely to occur, an operator manually sets a bridge inspection point Pb indicated by the dotted lines, which is extended to electrode pads adjacent to an inspection point Pa for observing the electrode pads 1A, 1B, 1C, . . . . There is no need for setting the bridge inspection point Pb between electrode pads having a large pad-to-pad distance D, and it is only necessary to set the inspection point Pa at which the state of the cream solder S on each electrode pad is observed.

Consequently, if an operator performs an inspection without making any manual setting, despite a defect due to a solder bridge, this may be detected as another kind of defect, or maybe even overlooked.

In addition, there are the following limitations: with respect to a solder bridge inspection region, it is required to indicate the inspection point Pb individually as above described; and the inspection point Pb can be pasted (copied) only to the same pattern on the component mounting board B. Thus, a considerable amount of time is required for creating data designating a solder bridge inspection region (an inspection point) Pb.

SUMMARY OF THE INVENTION

The present invention has been conceived in view of the above-mentioned problems, and a preferred embodiment of the present invention provides a component mounting board inspecting apparatus, which can automatically set a solder bridge inspection region (an inspection point) and output an optimum inspection result of a solder bridge.

According to a preferred embodiment of the present invention, a component mounting board inspecting apparatus for inspecting a solder bridge of an electronic circuit board, in which a plurality of electrode pads are formed at predetermined spaced intervals and cream solder is applied on the electrode pads, includes a mechanism for automatically determining the distance between adjacent electrode pads and a mechanism for automatically setting a solder bridge inspection point if the distance between adjacent electrode pads is equal or shorter than a set predetermined threshold value.

According to another preferred embodiment of the present invention, a component mounting board inspecting apparatus includes: an illuminating unit adapted to illuminate a component mounting board on which a plurality of electrode pads are formed at spaced intervals; an imaging device adapted to image-capture the illuminated component mounting board and outputting image data; a binarizer adapted to binarize the image data; a binarized image storage unit adapted to store the binarized image; a position coordinate acquiring unit adapted to acquire a position coordinate of each of the electrode pads from the stored binarized image; a near distance measuring unit adapted to measure a pad-to-pad distance of an electrode pad adjacent to the position coordinate of each of the electrode pads; a comparator adapted to compare the pad-to-pad distance with a threshold value; and a solder bridge inspection point setting unit adapted to set a solder bridge inspection point if the pad-to-pad distance is shorter than the threshold value.

Therefore, in accordance with the component mounting board inspecting apparatus of a preferred embodiment of the present invention, a solder bridge inspection point (region) can be set automatically. Because of this, an operator is able to output an optimum inspection result without spending the labor and the time involved in manual setting.

Additionally, in a variety of component mounting boards in which it is expected that there will be further complication, optimum setting of a solder bridge inspection point (region) is attainable only by setting a threshold value.

BRIEF DESCRIPTION OF THE DRAWINGS

The above and other objects, features and advantages of the present invention will become more apparent from the following description of the presently-preferred exemplary embodiments of the invention taken in conjunction with the accompanying drawings, in which.

DESCRIPTION OF THE PREFERRED EMBODIMENTS

Example of a Preferred Embodiment of the Present Invention

A component mounting board inspecting apparatus of a preferred embodiment of the present invention will be described with reference to the drawings.

Figure 1:
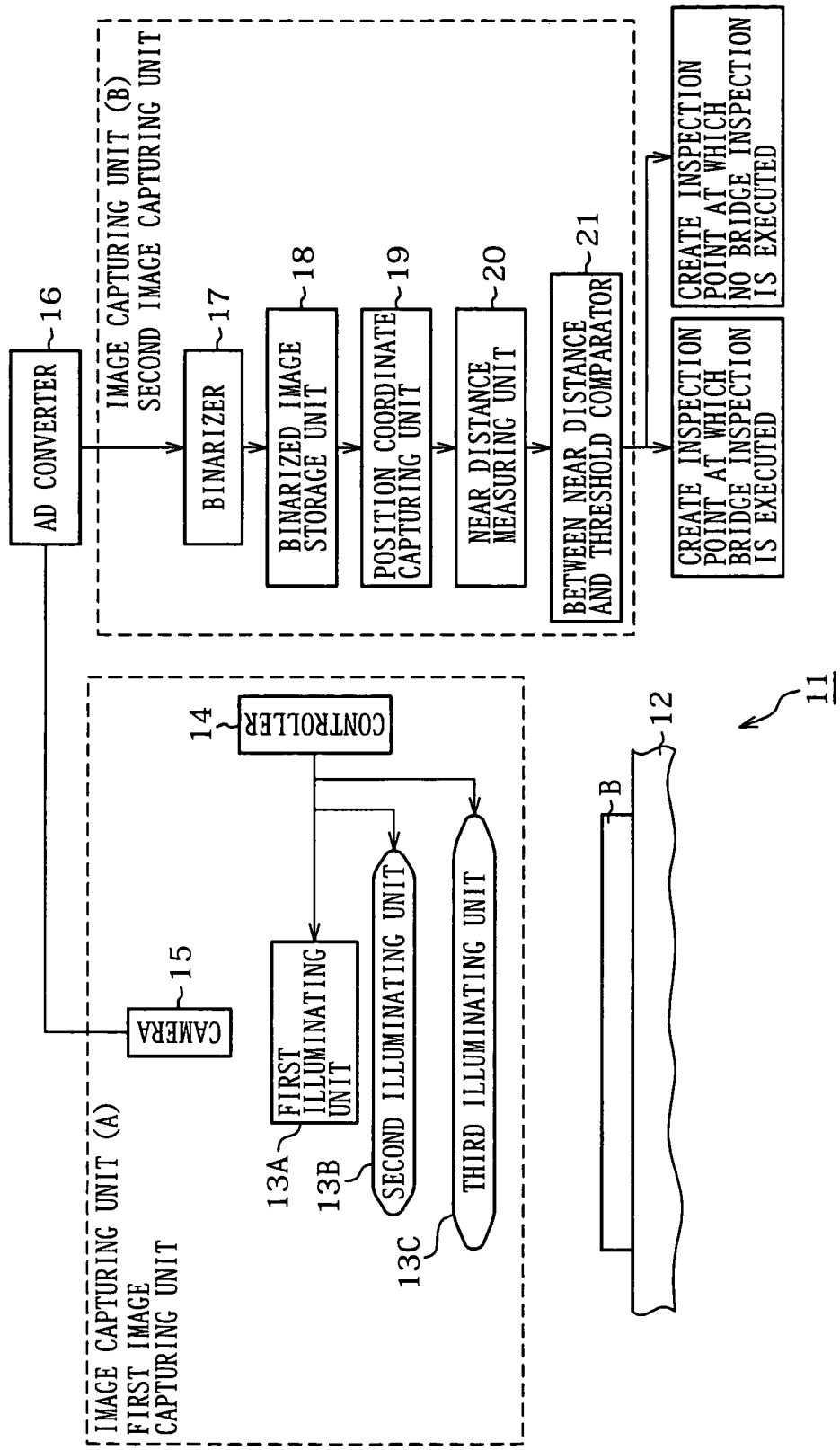
FIG. 1 is a schematic functional block diagram of a component mounting board inspecting apparatus of a preferred embodiment of the present invention.
Figure 2:
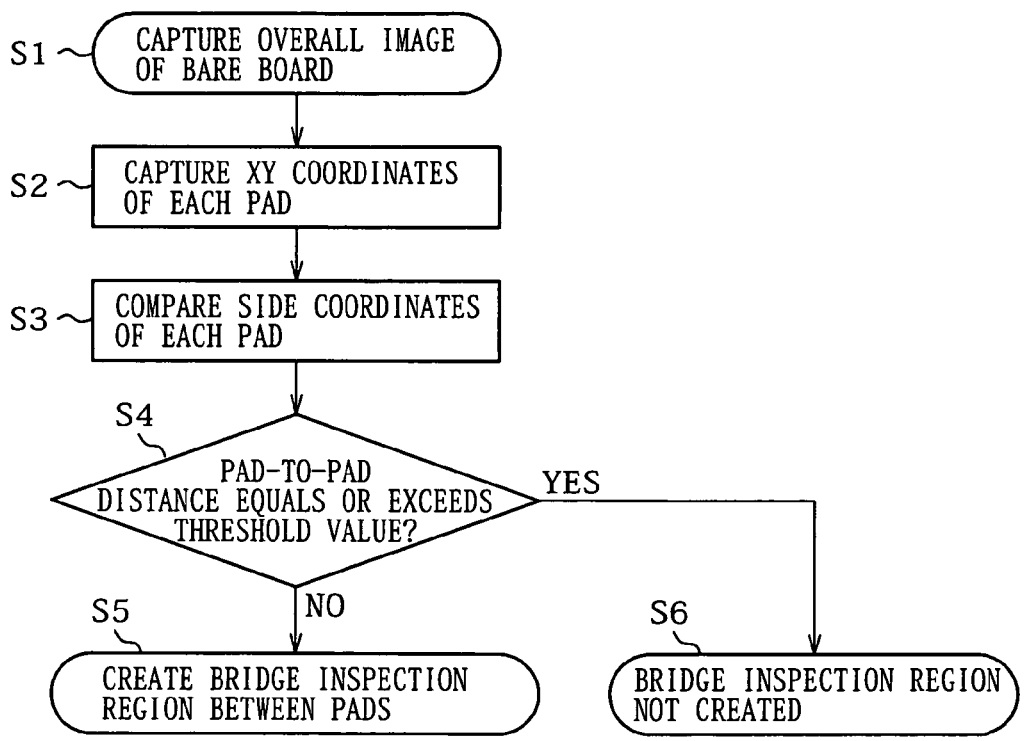
FIG. 2 is a flowchart showing a procedure to set a solder bridge inspection point in a preferred embodiment of the present invention.
Figure 3:
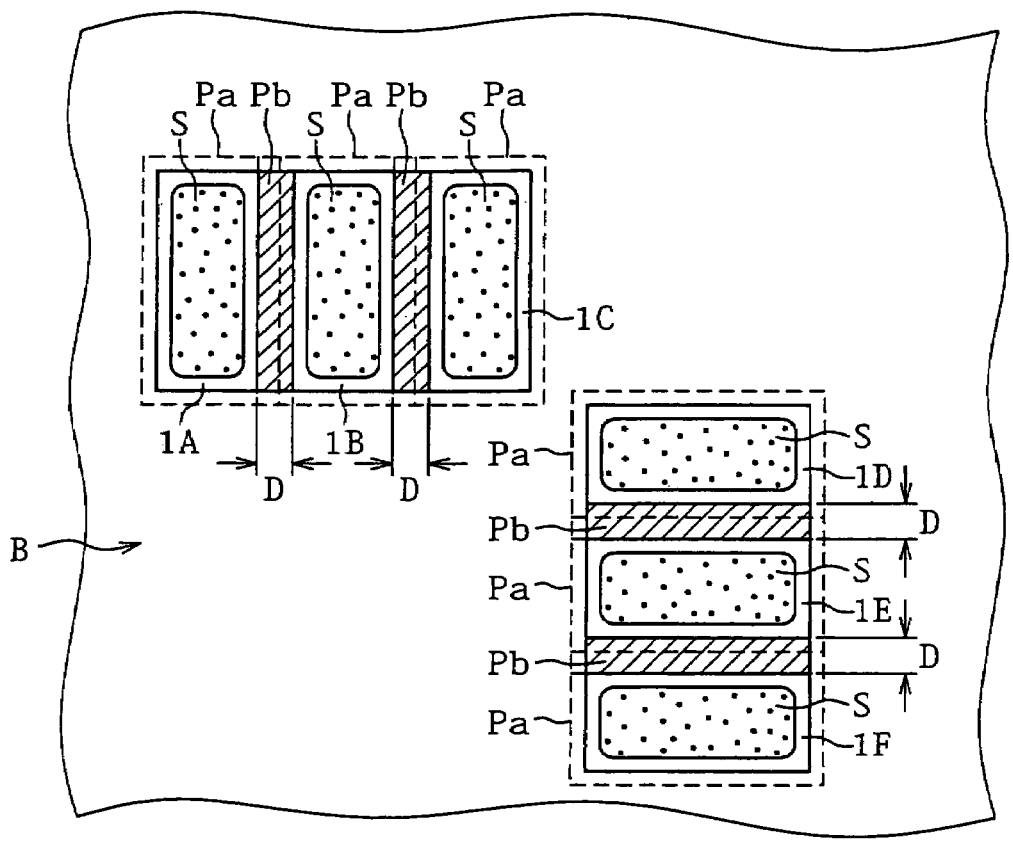
FIG. 3 is a plan view partially showing an electrode pad array having a short pad-to-pad distance, for the purpose of explaining the setting of a solder bridge inspection point.
Figure 4:
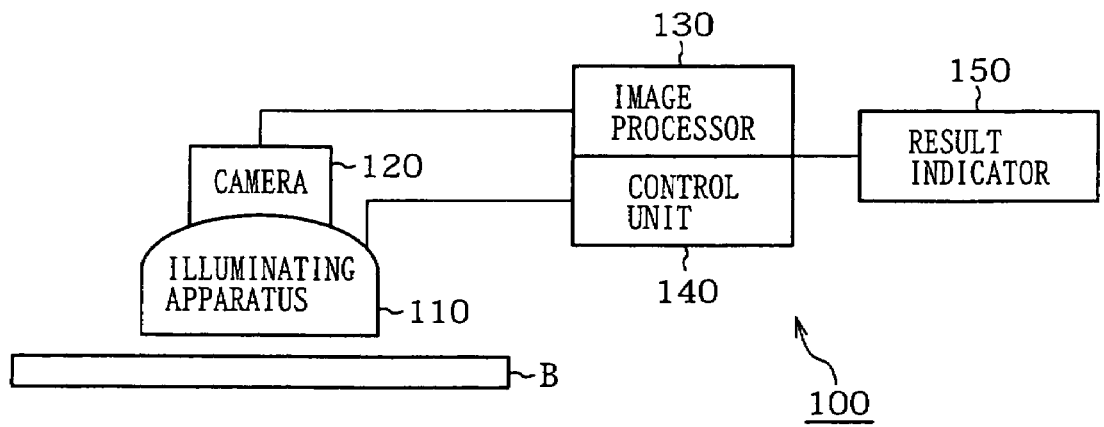
FIG. 4 is a functional block diagram of a component mounting board inspecting apparatus.

FIG. 1 is a schematic functional block diagram of a component mounting board inspecting apparatus of a preferred embodiment of the present invention. FIG. 2 shows a flowchart showing a procedure to set a solder bridge inspection point in a preferred embodiment of the present invention. FIG. 3 is a plan view partially showing an electrode pad array having a short pad-to-pad distance, for the purpose of explaining the setting of a solder bridge inspection point.

Referring now to FIG. 1, a description will be given of a component mounting board inspecting apparatus 11 of a preferred embodiment of the present invention.

In FIG. 1, reference numeral 11 indicates this component mounting board inspecting apparatus. The component mounting board inspecting apparatus 11 can be broadly classified into an image capturing unit (A) and an image processor (B).

A component mounting board (a so-called bare board) Bb, on which cream solder S to be inspected is not printed, is situated on a table 12.

The image capturing unit (A) is composed of a first illuminating unit 13A for irradiating a predetermined irradiation light to the component mounting board Bb, along the normal to the bottom surface of the component mounting board Bb; a second illuminating unit 13B for irradiating predetermined irradiation light to the component mounting board Bb, in the direction in which a predetermined angle is formed with the normal, and irradiating from the surroundings of the component mounting board Bb; a third illuminating unit 13C for irradiating the component mounting board Bb with irradiation light making a further greater angle than the predetermined angle to the normal of the second illuminating unit 13B; and a camera 15 disposed in the normal to the bottom surface of the component mounting board Bb. The camera 15 captures, as an image, the reflected light from the surface of the component mounting board Bb, which is derived from the irradiation light emitted from at least one selected from the first illuminating unit 13A, the second illuminating unit 13B, and the third illuminating unit 13C.

An analog signal outputted from the camera 15 is subjected to AD conversion by an analog/digital (AD) converter 16 for converting to a digital signal, and the digital signal is inputted to the image processor (B). The image processor (B) includes a binarizer 17, a binarized image storage unit 18, a position coordinate acquiring unit 19, a near distance measuring unit 20, and a comparator 21 for comparing a near distance with a threshold value.

Fetched as characteristic values of the component mounting board Bb are the area and the position (x-y coordinates) of each electrode pad on the component mounting board Bb. Therefore, the respective characteristic values are detected in association with the area and the position of a region on the image formed by the location where there is irradiation light having an intensity at least equal to or higher than a predetermined level.

The first illuminating unit 13A may be any one that is constructed such that illumination is irradiated uniformly from above the normal of the component mounting board Bb to the component mounting board Bb around approximately the center of the component mounting board Bb.

The second illuminating unit 13B may be any one that is constructed to irradiate light from obliquely above the component mounting board Bb and have its reflected light enter the camera 15.

The third illuminating unit 13C is preferably constructed to irradiate inspection light to the component mounting board Bb from the direction in which there is formed a greater angle than the angle defined between the normal direction of the component mounting board Bb of the second illuminating unit 13B and the above-mentioned obliquely-above direction. Although the angle thereof is not particularly limited, it is preferably constructed to irradiate from obliquely above, which is as horizontal as possible to the component mounting board Bb.

The first illuminating unit 13A, the second illuminating unit 13B and the third illuminating unit 13C can be driven independently or simultaneously, and depending on the type of the component mounting board Bb to be inspected, any one of these units is usable. A controller 14 is disposed to control the illuminating units 13A, 13B and 13C.

On the other hand, the camera 15 is preferably disposed substantially above the component mounting board Bb, such that the central optical axis of the camera 15 is arranged on the normal line of substantially the center of the component mounting board Bb. The camera 15 is also preferably a camera that can capture the reflected light from the component mounting board Bb as image information. For example, a CCD camera is usable.

In the component mounting board inspecting apparatus 11, the illuminating units and the camera 15 move integrally to underneath the controller 14, and a large number of points to be inspected, for example, as many as 4000 points, are sequentially scanned under a predetermined program. Then, the analog information outputted from the camera 15 is inputted, via the AD converter 16 for converting to digital information, to the image processor (B) for executing a predetermined image processing. Based on the digital signal from the AD converter 16, the image processor (B) selects and extracts the reflected light indicating a reflected light intensity exceeding a predetermined reference value, from the reflected lights reflected from the surface of the component mounting board Bb, and then creates an image indicating the location of the component mounting board Bb, from which the reflected light indicating the reflected light intensity exceeding the predetermined reference value is generated.

Specifically, the image processor (B) includes the binarizer 17 for executing binarization by applying a predetermined threshold value to inputted digital information; the binarized image storage unit 18 for creating and storing an image based on the binarized data obtained from the binarizer 17; the position coordinate acquiring unit 19 for acquiring the position (x-y coordinates) data of each electrode pad from the binarized image data stored in the binarized image storage unit 18; the near distance measuring unit 20 for measuring a pad-to-pad distance (a near distance) of adjacent electrode pads from the position (x-y coordinates) data of each electrode pad; and the between near distance and threshold comparator 21 for comparing the measured pad-to-pad distance with a threshold value manually initialized by an operator, etc.

Figure 5:
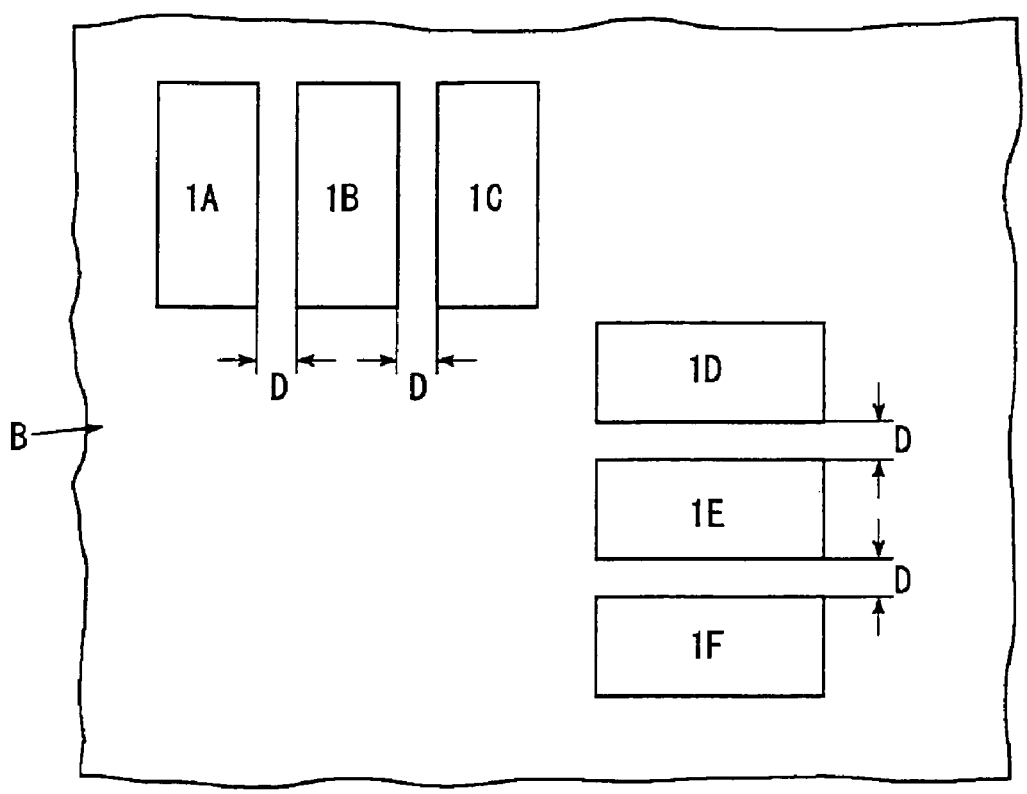
FIG. 5 is a plan view partially showing a component mounting board (a bare board) on which electrode pads are formed at short pad-to-pad distances.
Figure 6:
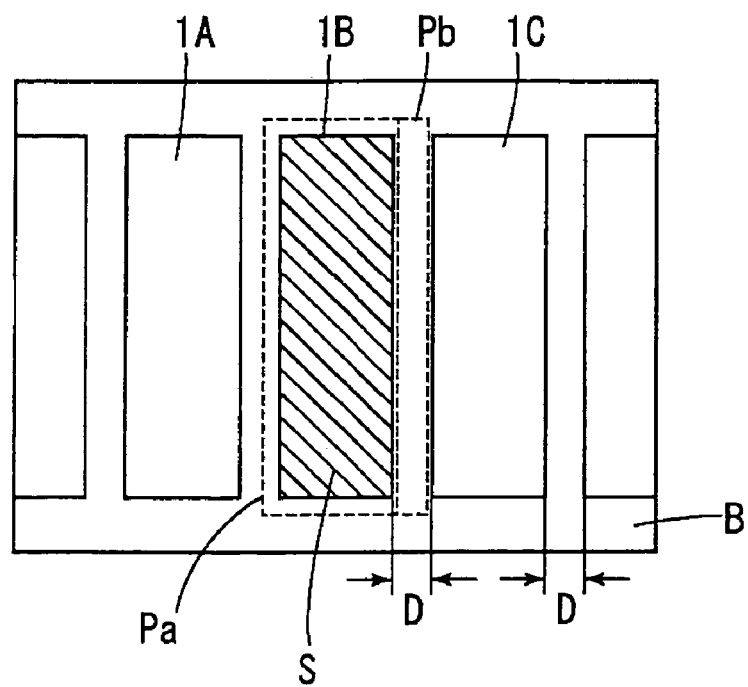
FIG. 6 is a plan view partially showing a component mounting board in which cream solder is suitably printed.

The initialized threshold value is the distance that can be judged as being susceptible to a solder bridge of the pad-to-pad distance D of each electrode pad formed on the component mounting board Bb. For example, based on the background information that the pad-to-pad distance D of the electrode pads 1A, 1B, 1C, . . . , which mount the BGA-type IC and the QFP-type IC as shown in FIG. 5, is considerably short, and the pad-to-pad distance is as short as about 500 µm, as above described, the value of 500 µm is initialized as a threshold value.

The operation of the component mounting board inspecting apparatus 11 will be described next with reference to FIG. 2 and FIG. 3.

First, the component mounting board (bare board) Bb, in which cream solder is not printed on electrode pads, etc., is situated and secured to the table 12. Then, the irradiation light from any one of the illuminating units, for example, the second illuminating unit 13B, is irradiated sequentially from obliquely above to the respective electrode pads of the component mounting board Bb. Then, the binarizer 17 binarizes their respective images, and their binarized images are written in the binarized image storage unit 18 (step S1).

Subsequently, the position coordinate acquiring unit 19 captures the coordinates in the X-axis direction and the Y-axis direction of the respective electrode pads (step S2), and the near distance measuring unit 20 measures the side coordinates of the respective electrode pads, that is, the pad-to-pad distance of adjacent electrode pads.

The between near distance and threshold comparator 21 compares the pad-to-pad distance (the near distance) measured by the near distance measuring unit 20 with a previously initialized threshold value, for example, 500 µm (step S4). When the pad-to-pad distance is shorter than the threshold value, a solder bridge inspection point Pb, at which solder bridge inspection is executed, (the hatching area) is created (step S5). If the pad-to-pad distance is equal or larger than the threshold value, the solder bridge inspection point Pb, at which solder bridge inspection is executed, is not created, and only an inspection point Pa is created (step S6).

When creating the solder bridge inspection point Pb, as shown in FIG. 3, the solder bridge inspection point Pb is created only on the right side of the respective electrode pads 1A, 1B, 1C, . . . and on the upper side of the respective electrode pads 1D, 1E, F, . . . . It is set such that an operator will be informed by speech generation of a "solder bridge defect on the right side," and a "solder bridge defect on the upper side" at each inspection point. Herein, the pad-to-pad distance D is shorter than the threshold value.

Figure 7:
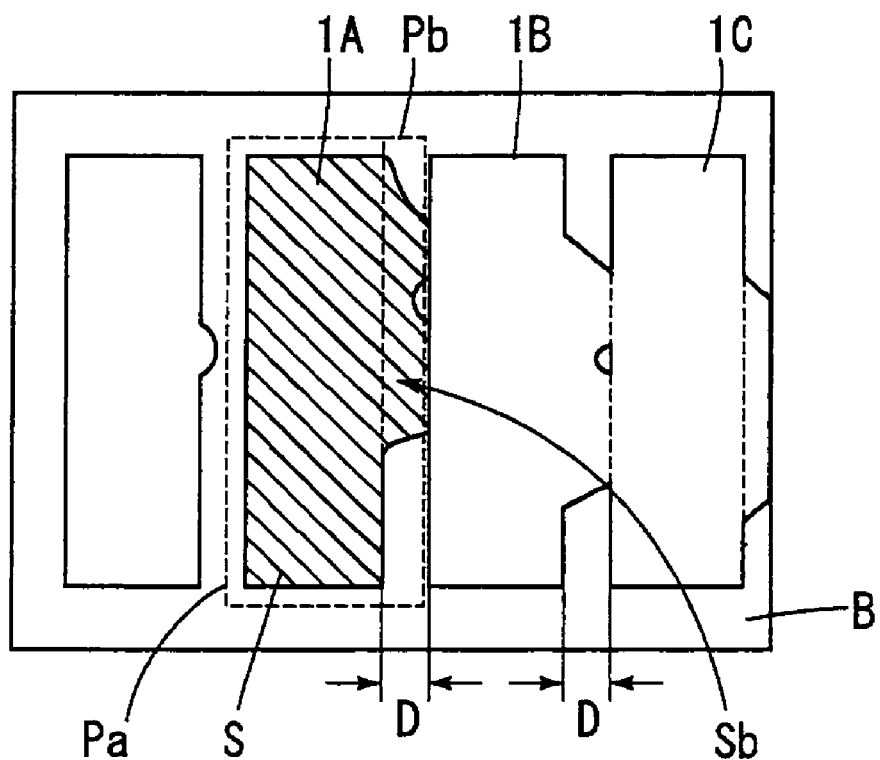
FIG. 7 is a plan view partially showing a component mounting board in which cream solder is printed, causing the occurrence of a solder bridge.

Thus, by virtue of the automatic setting of the solder-bridge inspection point in the component mounting board inspecting apparatus 11, the component mounting board Bb, in which cream solder is printed on each electrode pad, is situated on the table 12, and the image capturing unit (A) is moved sequentially as above described, and then the camera 15 captures the image under illumination of any one of the illuminating units. When a portion smaller than the threshold value of the pad-to-pad distance D is detected, the solder bridge inspection point Pb is expanded automatically between the pads, and it is detectable whether the solder bridge Sb is generated or not, as shown in FIG. 7. If the solder bridge Sb is detected, the cream solder portion thereof may be colored red, for example, in order to let an operator easily recognize this on the image indicator.

Therefore, according to the example of the embodiment of a component mounting board inspecting apparatus of the present invention, the inspection point for the solder bridge may be automatically set and, as a result, the operator may output a desirable inspection result without spending time or requiring an effort for manually setting the point.

Though a preferred embodiment of the present invention has been described herein in its preferred form through examples of preferred embodiments thereof with a certain degree of particularity, the present invention should not be construed as to be limited to such examples of preferred embodiments presented herein, so that various modifications, variations, combinations, and sub-combinations as well as different applications thereof are possible without departing from the scope of this invention. For example, though reference has been made in the preferred embodiments to a camera to work as an imaging device, many other types of imaging apparatuses or devices may be used, such as imaging elements or other elements that would function to capture light for imaging purposes or capturing signals and/or information for similar purposes.

What is claimed is:

1. An inspecting apparatus for inspecting for a solder bridge between electrode pads on a component mounting board and for determining whether inspection for the solder bridge is to be executed, the apparatus comprising:
   a mechanism configured to store a predetermined threshold value representing an operator's selected distance between adjacent electrode pads, the predetermined threshold value being manually inputted by an operator, a mechanism configured to determine an actual distance between adjacent electrode pads in a first direction and a second direction, the second direction being orthogonal to the first direction; and a mechanism configured to create a solder bridge inspection point and if the actual distance between the adjacent electrode pads in either the first direction or the second direction is shorter than the predetermined threshold value, then inspection for the solder bridge is executed at the solder bridge inspection point and if the actual distance between the adjacent electrode pads in either the first direction or the second direction is greater than or equal to the threshold value, then inspection for the solder bridge is not executed.

2. The inspecting apparatus of claim 1, wherein the mechanism configured to determine a distance between electrode pads includes:

a first illuminating unit which irradiates a predetermined irradiation light onto the component mounting board at an angle parallel to the normal of the bottom surface of the component mounting board;

a second illuminating unit which irradiates a predetermined irradiation light onto the component mounting board from a first angle from said normal; and a third illuminating unit which irradiates a predetermined irradiation light onto the component mounting board from a second angle from said normal;

wherein the second angle from the normal is greater than the first angle from the normal.

3. The inspecting apparatus of claim 2, wherein the mechanism configured to determine a distance between electrode pads includes:

an image capture device which captures image data from the light emitted from the first illuminating unit, the second illuminating unit, or the third illuminating unit and reflected from the surface of the component mounting board.

4. A component mounting board inspecting apparatus for inspecting for a solder bridge between electrode pads on a component mounting board and for determining whether inspection for the solder bridge is to be executed, the component mounting board inspecting apparatus comprising:

an illuminating device adapted to illuminate a component mounting board on which a plurality of electrode pads is formed at spaced intervals;

an imaging device adapted to image-capture the illuminated component mounting board and outputting image data;

a binarizer adapted to binarize the image data;

a binarized image storage unit adapted to store the binarized image;

a position coordinate acquiring unit adapted to acquire position coordinates of each of the electrode pads from the stored binarized image;

a near distance measuring unit adapted to measure a pad-to-pad distance of an electrode pad adjacent to the position coordinate of each of the electrode pads in a first direction or a second direction, the second direction being orthogonal to the first direction;

a mechanism configured to store a predetermined threshold value representing an operator's selected distance between adjacent electrode pads, the predetermined threshold value being manually inputted by an operator, a comparator adapted to compare the pad-to-pad distance with the predetermined threshold value; and a solder bridge inspection point setting unit adapted to set a solder bridge inspection point and if said pad-to-pad distance between said adjacent electrode pads in either the first direction or the second direction is shorter than the predetermined threshold value, then inspection for the solder bridge is executed at the solder bridge inspection point and if said actual distance between said adjacent electrode pads in either the first direction or the second direction is greater than or equal to the threshold value, then inspection for the solder bridge is not executed.

5. The component mounting board inspecting apparatus of claim 4, wherein the illuminating device includes:

a first illuminating unit which irradiates a predetermined irradiation light onto the component mounting board at an angle parallel to the normal of the bottom surface of the component mounting board;

a second illuminating unit which irradiates a predetermined irradiation light onto the component mounting board from a first angle from said normal; and a third illuminating unit which irradiates a predetermined irradiation light onto the component mounting board from a second angle from said normal;

wherein the second angle from the normal is greater than the first angle from the normal.

6. The component mounting board inspecting apparatus of claim 5, wherein the imaging device captures image data from the light emitted from the first illuminating unit, the second illuminating unit, or the third illuminating unit and reflected from the surface of the component mounting board.

7. A computer-implemented method for inspecting a component mounting board for solder bridges, the computer-implemented method comprising the steps of:

predetermining a threshold value representing an operator's selected distance between adjacent electrode pads;

determining a distance between adjacent electrode pads on the component mounting board in both a first direction and a second direction, the second direction being orthogonal to the first direction;

setting a solder bridge inspection point between adjacent electrode pads; and if the distance between said adjacent electrode pads in either the first direction or second direction is shorter than the threshold value, then executing inspection for the solder bridge at the solder bridge inspection point and, if said distance between said adjacent electrode pads in either the first direction or the second direction is greater than or equal to the threshold value, then abstaining from inspection for the solder bridge.

8. The computer-implemented method for inspecting a component mounting board for solder bridges of claim 7 wherein the step of determining the distance between adjacent electrode pads includes:

illuminating the component mounting board with a predetermined irradiation light from a direction parallel to the normal of the bottom surface of the component mounting board;

illuminating the component mounting board with a predetermined irradiation light from a direction at a first angle from said normal; and illuminating the component mounting board with a predetermined irradiation light from a direction at a second angle from said normal;

wherein the second angle from the normal is greater than the first angle from the normal.

* * * * *